United States Patent [19]

Watts

[11] Patent Number: 4,499,099

[45] Date of Patent: Feb. 12, 1985

[54] NORTROPANE AND GRANATANE TYPE COMPOUNDS USEFUL IN TREATING PSYCHOSIS

[75] Inventor: Eric A. Watts, Harlow, England

[73] Assignee: Beecham Group p.l.c., England

[21] Appl. No.: 386,723

[22] Filed: Jun. 9, 1982

[30] Foreign Application Priority Data

| Jun. 17, 1981 | [GB] | United Kingdom | 8118603 |
| Jun. 17, 1981 | [GB] | United Kingdom | 8118604 |
| Jun. 29, 1981 | [GB] | United Kingdom | 8119997 |
| Jun. 29, 1981 | [GB] | United Kingdom | 8119998 |
| Dec. 15, 1981 | [GB] | United Kingdom | 8137821 |

[51] Int. Cl.³ ............... A61K 31/46; C07D 451/02; C07D 451/14

[52] U.S. Cl. ............... 514/299; 260/244.4; 260/245.7; 260/239 BF; 546/112; 546/124; 546/125; 546/126; 548/452; 514/304

[58] Field of Search ............... 546/124, 125, 126, 112; 260/244.4, 245.7, 239 BF; 548/452; 424/265, 267

[56] References Cited

U.S. PATENT DOCUMENTS

| 4,273,778 | 6/1981 | Hadley et al. ............... 424/265 |
| 4,350,691 | 9/1982 | Hadley et al. ............... 546/124 |
| 4,434,170 | 2/1984 | Dostert et al. ............... 546/124 |

FOREIGN PATENT DOCUMENTS

| 13138 | 7/1980 | European Pat. Off. |
| 42705 | 12/1981 | European Pat. Off. |
| 2446823 | 8/1980 | France |
| 2476088 | 8/1981 | France |
| 2042522 | 9/1980 | United Kingdom |

Primary Examiner—Henry R. Jiles
Assistant Examiner—Bernard I. Dentz
Attorney, Agent, or Firm—Jacobs & Jacobs

[57] ABSTRACT

Pharmaceutical compositions comprising compounds of formula (I) or pharmaceutically acceptable salts and/or N-oxides and/or solvates thereof:

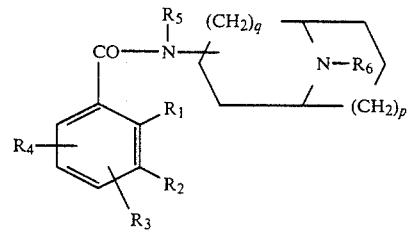

wherein:

$R_1$ is a $C_{1-6}$ alkoxy or $C_{1-6}$ alkylthio group; and
one of $R_2$, $R_3$ and $R_4$ is hydrogen, the second is $C_{1-6}$ alkylthio and the third is selected from the class of substituents consisting of hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonyl, $C_{1-6}$ alkylsulphinyl, hydroxy, nitro or amino, aminocarbonyl or aminosulphonyl optionally N-substituted by one or two $C_{1-6}$ alkyl groups; or
$R_1$ is joined to $R_2$ to form $C_{1-2}$ alkylenedioxy; and
one of $R_3$ and $R_4$ is $C_{1-6}$ alkylthio and the other is selected from the class of substituents defined above;
$R_5$ is hydrogen or $C_{1-6}$ alkyl;
$R_6$ is $C_{1-7}$ alkyl or a group $-(CH_2)_sR_7$ where s is 0 to 2 and $R_7$ is a $C_{3-8}$ cycloalkyl group, or a group $-(CH_2)_tR_8$ where t is 1 or 2 and $R_8$ is $C_{2-5}$ alkenyl or a phenyl group optionally substituted by one or two substituents selected from $C_{1-6}$ alkyl, $C_{1-4}$ alkoxy, trifluoromethyl and halogen, or a thienyl group; and
p and q are independently 0 to 2 and a pharmaceutically acceptable carrier, novel compounds within formula (I) having useful pharmacological activity and a process for their preparation. The compounds are useful in the treatment of psychosis.

10 Claims, No Drawings

NORTROPANE AND GRANATANE TYPE COMPOUNDS USEFUL IN TREATING PSYCHOSIS

This invention relates to novel compounds, to novel pharmaceutical compositions containing these and other compounds and to a process for the preparation of such compounds.

European Patent Application No. 79302978.6 and U.S. Pat. No. 4,273,778 disclose that compounds of the formula (A), and pharmaceutically acceptable salts thereof:

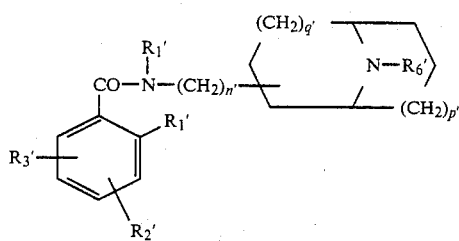

wherein:

$R_1'$ is a $C_{1-6}$ alkoxy group;

$R_2'$ and $R_3'$ are the same or different and are hydrogen, halogen, $CF_3$, $C_{2-7}$ acyl, $C_{2-7}$ acylamino, or amino, aminocarbonyl or aminosulphone optionally substituted by one or two $C_{1-6}$ alkyl groups, $C_{1-6}$ alkylsulphone or nitro;

$R_5'$ is hydrogen or $C_{1-6}$ alkyl;

$R_6'$ is $C_{1-7}$ alkyl or a group —$(CH_2)_s'R_7'$ where s' is 0 to 2 and $R_7'$ is a $C_{3-8}$ cycloalkyl group, or a group —$(CH_2)_{t'}R_8'$ where t' is 1 or 2 and $R_8'$ is $C_{2-5}$ alkenyl or a phenyl group optionally substituted by one or two substituents selected from $C_{1-6}$ alkyl, $C_{1-4}$ alkoxy, trifluoromethyl and halogen; and n', p' and q' are independently 0 to 2; have useful pharmacological activity. More specifically the compounds of formula (A) are stated to be useful in the treatment of disorders related to impaired gastro-intestinal motility and/or in the treatment of disorders of the central nervous system. All the compounds are stated to have anti-emetic activity.

European Patent Application No. 81302630.9 discloses compounds of formula (B) and pharmaceutically acceptable salts thereof:

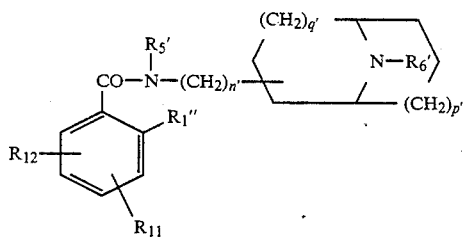

wherein:

$R_1''$ is a $C_{1-6}$ alkoxy or $C_{1-6}$ alkylthio group;

$R_{11}$ is hydrogen, amino or $C_{1-7}$ acylamino;

$R_{12}$ is $C_{1-6}$ alkylsulphinyl;

and the remaining variables are as defined in formula (A), except that an additional value for $R_6'$ is thienyl. These compounds are described as having dopamine antagonist activity.

Compounds of formula (B) wherein $R_{12}$ is replaced by a $C_{1-6}$ alkylthio group are mentioned as possible intermediates in the preparation of the compounds of formula (B).

It has now been discovered that a group of compounds structurally distinct from those of formulae (A) and (B), having an alkylthio benzamide substituent, also have pharmacological activity in particular, dopamine antagonist activity.

Accordingly, the present invention provides a pharmaceutical composition comprising a compound of formula (I) or a pharmaceutically acceptable salt and/or N-oxide and/or solvate thereof:

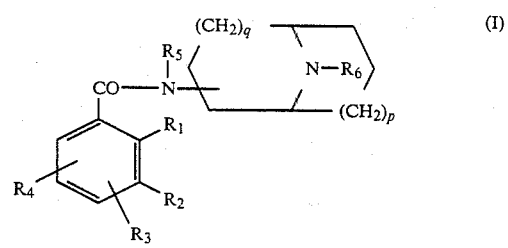

wherein:

$R_1$ is a $C_{1-6}$ alkoxy or $C_{1-6}$ alkylthio group; and one of $R_2$, $R_3$ and $R_4$ is hydrogen, the second is $C_{1-6}$ alkylthio and the third is selected from the class of substituents consisting of hydrogen, halogen, $CF_3$, $C_{1-6}$ alkyl, $C_{1-6}$ alkoxy, $C_{1-6}$ alkylthio, $C_{1-7}$ acyl, $C_{1-7}$ acylamino, $C_{1-6}$ alkylsulphonyl, $C_{1-6}$ alkylsulphinyl, hydroxy, nitro or amino, aminocarbonyl or aminosulphonyl optionally N-substituted by one or two $C_{1-6}$ alkyl groups; or $R_1$ is joined to $R_2$ to form $C_{1-2}$ alkylenedioxy; and one of $R_3$ and $R_4$ is $C_{1-6}$ alkylthio and the other is selected from the class of substituents defined above;

$R_5$ is hydrogen or $C_{1-6}$ alkyl;

$R_6$ is $C_{1-7}$ alkyl or a group —$(CH_2)_sR_7$ where s is 0 to 2 and $R_7$ is a $C_{3-8}$ cycloalkyl group, or a group —$(CH_2)_tR_8$ where t is 1 or 2 and $R_8$ is $C_{2-5}$ alkenyl or a phenyl group optionally substituted by one or two substituents selected from $C_{1-6}$ alkyl, $C_{1-4}$ alkoxy, trifluoromethyl and halogen, or a thienyl group; and p and q are independently 0 to 2 and a pharmaceutically acceptable carrier.

The invention also provides a process for the preparation of a pharmaceutical composition comprising the admixture of a compound of formula (I), or a pharmaceutically acceptable salt, and/or a solvate and/or an N-oxide thereof and a pharmaceutically acceptable carrier.

Such compositions are suitably adapted for oral or parental administration, and as such may be in the form of tablets, capsules, oral liquid preparations, powders, granules, lozenges, reconstitutable powders, injectable and infusable solutions or suspensions or suppositories. Orally administerable compositions are preferred.

Tablets and capsules for oral administration are usually presented in a unit dose, and contain conventional excipients such as binding agents, fillers, tabletting agents, lubricants, disintegrants, and wetting agents. The tablets may be coated according to well known methods in the art. Oral liquid preparations are usually in the form of aqueous or oily suspensions, solutions, emulsions, syrups, or elixirs or are presented as a dry product for reconstitution with water or other suitable vehicle before use. Such liquid preparations may contain conventional additives such as suspending agents, emulsifying agents, non-aqueous vehicles (which may include edible oils), preservatives, and flavouring or colouring agents.

For parenteral administration, fluid unit dose forms are prepared containing a compound of the present invention and a sterile vehicle. The compound, depending on the vehicle and the concentration, can be either suspended or dissolved. Parenteral solutions are normally prepared by dissolving the compound in the vehicle and filter sterilizing before filling into a suitable vial or ampoule and sealing. Advantageously, adjuvants such as a local anaesthetic, preservatives and buffering agents are also dissolved in the vehicle.

Parental suspensions are prepared in substantially the same manner except that the compound is suspended in the vehicle instead of being dissolved and sterilized by exposure to ethylene oxide before suspending in the sterile vehicle. Advantageously, a surfactant or wetting agent is included in the composition to facilitate uniform distribution of the compound of the invention.

The invention further provides a method of treatment of disorders in mammals, such as humans, which comprises the administration of an effective amount of a compound of the formula (I), or a pharmaceutically acceptable salt thereof, and/or an solvate and/or N-oxide thereof, or a pharmaceutical composition, as hereinbefore defined to the sufferer.

An amount effective to treat the disorders hereinbefore described depends on the relative efficacies of the compounds of the invention, the nature and severity of the disorder being treated and the weight of the mammal. However, a unit dose will normally contain 0.1 to 20 mg for example 0.5 to 10 mg, of the compound of the invention. Unit doses will normally be administered more than once a day, for example 2, 3, 4, 5 or 6 times a day such that the total daily dose is normally in the range 0.01 to 10 mg/kg per day. The compounds of the present invention have the ability to potentiate the effect of conventional analgesics in migraine treatment when administered concurrently with the analgesic.

Accordingly, the present invention also provides a pharmaceutical composition comprising a compound of the formula (I) and an analgesic.

The compound of the formula (I) and the analgesic, such as aspirin or paracetamol, are present in the composition in amounts generally similar to their usual effective dose.

The composition can be a combination product, for example a tablet or capsule containing both a compound of the invention and an analgesic for oral administration, or a twin pack comprising the two active ingredients made up for separate administration.

The invention accordingly provides a method of treatment of migraine comprising the administration of an effective amount of a compound of the formula (I) and an analgesic.

The invention also provides a compound of formula (I), for use in the treatment of emesis, disorders relating to impaired gastro-intestinal motility and of disorders of the central nervous system.

The invention also provides a pharmaceutically acceptable salt and/or solvate and/or N-oxide of a compound of formula (I). The invention further provides a process for preparing a pharmaceutically acceptable salt and/or solvate and/or N-oxide of a compound of formula (I).

Salts, hydrates and N-oxides of the compounds of formula (I) may be formed conventionally. The salts may be formed for example by reaction of the base compound of formula (I) with a pharmaceutically acceptable organic or inorganic acid.

N-oxides of the nitrogen atom of the bicyclic ring system are produced by reaction of a compound of formula (I) with an organic peracid, such as m-chloroperbenzoic acid in, for example, a chlorinated hydrocarbon solvent at below ambient temperature.

Quaternary ammonium salts may be prepared by reaction of a compound of the present invention with the appropriate alkyl, aryl, aralkyl chloride, bromide or iodide. This reaction may be carried out in a solvent, such as acetone methanol, ethanol, dimethylformamide at ambient or elevated temperature with or without pressure.

The compounds of the present invention are dopamine antagonists and may generally be used in the treatment of emesis. Depending on their balance between peripheral and central action on the nervous system, they may also be used in the treatment of disorders relating to impaired gastrointestinal motility, such as retarded gastric emptying, dyspepsia, flatulence, oesophagal reflux and peptic ulcer and/or in the treatment of disorders of the central nervous system, such as psychosis.

Those compounds of the present invention which are of particular interest for their beneficial effect on gastric motility are the quaternary ammonium salts of the compounds of formula (I). The compounds of formula (I) are of particular interest for treatment of disorders of the central nervous system.

With respect to formula (I), suitable examples of the group $R_1$ include methoxy, ethoxy and n- and iso-propoxy, methylthio, ethylthio, and n- and iso-propylthio. Preferably $R_1$ is a methoxy group.

Suitable examples of the second of $R_2$, $R_3$ and $R_4$ include methylthio, ethylthio, n- and iso-propylthio. Preferably the second of $R_2$, $R_3$ and $R_4$ is methylthio.

Suitable examples of the third of $R_2$, $R_3$ and $R_4$ include the following groups: hydrogen, chlorine, bromine, amino, $C_{1-4}$ alkanoylamino such as formylamino, acetylamino, propionylamino, n- and iso-butyrylamino, aminosulphonyl, and amino and aminosulphonyl substituted by one or two methyl, ethyl, n- or iso-propyl groups; n- and iso-propoxy, methylthio, ethylthio, n- and iso-propylthio and hydroxy.

Particularly suitable examples of the third of $R_2$, $R_3$ and $R_4$ include hydrogen, amino, $C_{1-4}$ alkanoylamino, methoxy and methylthio.

It is generally preferred that $R_3$ is in the 4-position relative to the bicycloalkyl(alkyl)acylamino side chain for greater activity in the resultant compound of the formula (I). For the same reason it is generally preferred that $R_4$ is in the 5-position relative to the same acylamino side chain. When the third of $R_2$, $R_3$ and $R_4$ is $C_{1-6}$ alkoxy, it is preferably $R_2$, and is methoxy.

Particularly preferred $R_3$ groups when $R_2$ is hydrogen include 4-amino and 4-(acylated amino), especially 4-acetylamino as defined. Preferably $R_3$ then is 4-amino or 4-acetylamino.

Particularly preferred $R_4$ groups include 5-alkylthio such as 5-methylthio. Other $R_4$ groups of interest include substituted 5-aminosulphonyl as defined and 5-

$C_{1-6}$ alkylsulphonyl or -sulphinyl, such as 5-aminosulphonyl and 5-methyl sulphonyl.

When $R_1$ and $R_2$ taken together are methylenedioxy or ethylenedioxy $R_1$ and $R_2$ are preferably ethylenedioxy.

Suitable examples of $R_5$ include hydrogen, methyl, ethyl, n- and iso-propyl, n-, sec-, iso- and tert-butyl, preferably hydrogen or methyl, in particular hydrogen.

Suitable examples of $R_6$ when $C_{1-7}$ alkyl include methyl, ethyl, n- and iso-propyl and n-, sec-, iso- and tert-butyl, n-pentyl, n-hexyl, n-heptyl and 3-methylbutyl, 4-methylpentyl and 5-methylhexyl.

Within $C_{1-7}$ alkyl radicals, $C_{1-4}$ alkyl are particularly useful.

Suitable examples of $R_6$ when $C_{1-4}$ alkyl include methyl, ethyl, n- and iso-propyl and n-, sec-, iso- and tert-butyl, particularly methyl, n-propyl and sec-butyl.

Similarly, within $C_{1-7}$ radicals, $C_{5-7}$ alkyl are also of interest.

Suitable examples of $R_6$ when $C_{5-7}$ alkyl include n-pentyl, n-hexyl and n-heptyl, 3-methylbutyl, 4-methylpentyl and 5-methylhexyl.

When $R_6$ is a group $-(CH_2)_s R_7$ as defined, suitable examples of $R_7$ include $C_{5-8}$ cycloalkyl, preferably cyclohexyl. s is preferably 1.

When $R_6$ is a group $-(CH_2)_t R_8$ as defined, t is preferably 1.

In such a group $R_6$, when $R_8$ is $C_{2-5}$ alkenyl, suitable examples thereof include vinyl, prop-1-enyl, prop-2-enyl, 1-methylvinyl, but-1-enyl, but-2-enyl, but-3-enyl, 1-methylenepropyl, 1-methylprop-1-enyl and 1-methylprop-2-enyl, in their E and Z forms where stereisomerism exists.

A preferred $C_{1-5}$ alkenyl $R_8$ radical is vinyl, so that $R_6$ is preferably allyl.

When $R_8$ is optionally substituted phenyl as defined above, suitable examples of such optional phenyl substituents include methyl, ethyl, n- and iso-propyl, n, sec- and tert-butyl; methoxy, ethoxy, n- and iso-propoxy; $CF_3$, fluoro, chloro or bromo. Preferably $R_8$ when optionally substituted phenyl is unsubstituted or 4-substituted by fluoro, chloro or methyl. When $R_8$ is thienyl it may be 2- or 3-thienyl, generally 2-thienyl.

Compounds of the formula (I) wherein $R_6$ is $-(CH_2)_t R_8$ as defined, are of particular interest because of their beneficial pharmacological activity.

p and q are suitably 0 to 1, preferably 1.

Often the amide and side chain nitrogen atoms are separated by a minimum of 2 or 3 carbon atoms, preferably 3. When the separation is 3 carbon atoms, the $CONR_5$ moiety is preferably in an equatorial orientation to the bicyclic system.

The invention also provides compounds within formula (I) of formula (II) and pharmaceutically acceptable salts and solvate and N-oxides thereof:

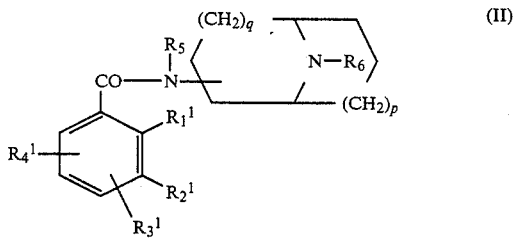

wherein:

$R_1^1$ is a $C_{1-6}$ alkoxy or $C_{1-6}$ alkylthio group; and one of $R_2^1$, $R_3^1$ and $R_4^1$ is hydrogen, the second is $C_{1-6}$ alkylthio and the third is selected from halogen, $CF_3$, $C_{1-6}$ alkyl, $C_{1-6}$ alkoxy, $C_{1-6}$ alkylthio, $C_{1-7}$ acyl, $C_{1-6}$ alkylsulphonyl, $C_{1-6}$ alkylsulphinyl, hydroxy, or aminocarbonyl or aminosulphonyl optionally N-substituted by one or more $C_{1-6}$ alkyl groups;

or $R_1^1$ is joined to $R_2^1$ to form $C_{1-2}$ alkylenedioxy; and one of $R_3^1$ and $R_4^1$ is $C_{1-6}$ alkylthio and the other is selected from the class of substituents defined in formula (I); and the remaining variables are as defined in formula (I).

Suitable and preferred values of $R_1^1$, $R_2^1$, $R_3^1$, $R_4^1$, $R_5$, $R_6$, p and q are essentially as hereinbefore described with reference to the corresponding variables in formula (I).

Favourably, the benzamide moiety in the compound of formula (II) is of formula (III):

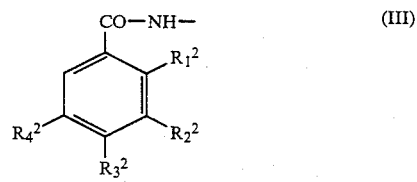

wherein:

$R_1^2$ is $C_{1-6}$ alkoxy;

one of $R_2^2$, $R_3^2$ and $R_4^2$ is hydrogen, the second is $C_{1-6}$ alkylthio and the third is $C_{1-6}$ alkoxy or $C_{1-6}$ alkylthio.

Preferably $R_2^2$ is $C_{1-6}$ alkoxy, $R_3^2$ is hydrogen and $R_4^2$ is $C_{1-6}$ alkylthio.

A particularly preferred moiety of formula (IV) is wherein $R_1^2$ is methoxy, $R_2^2$ is methoxy, $R_3^2$ is hydrogen and $R_4^2$ is methylthio.

A favourable group of compounds within formula (I) is therefore of formula (IV):

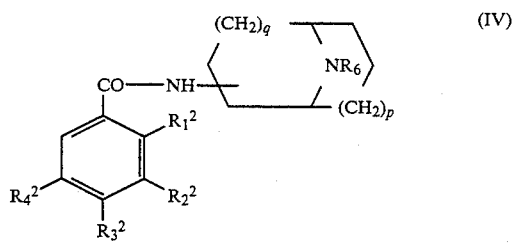

wherein the variables are as hereinbefore defined.

Suitable and preferred values for $R_6$, p and q are as described under formula (I). Preferably q is 1 and the moiety of formula (III) is then attached at the 3-position numbering through the $-(CH_2)_q$ containing ring from a bridgehead atom taken as 1 (not necessarily standard numbering).

Suitable and preferred values for $R_1^2$, $R_2^2$, $R_3^2$ and $R_4^2$ are as described under formula (III).

A sub-group of compounds within formula (IV) is of formula (V):

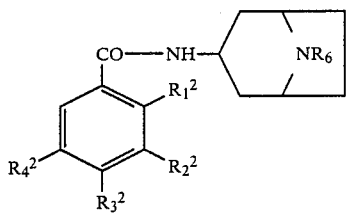 (V)

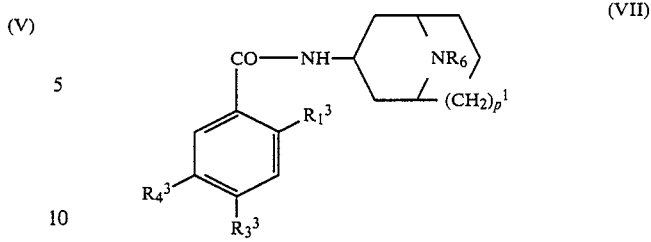 (VII)

wherein:
$R_1{}^2$, $R_2{}^2$, $R_3{}^2$, $R_4{}^2$ and $R_6$ are as hereinbefore defined.

Suitable and preferred values of $R_1{}^2$, $R_2{}^2$, $R_3{}^2$, $R_4{}^2$ and $R_6$ are as hereinbefore described in relation to formula (III). In particular, $R_6$ is unsubstituted benzyl.

It is preferred that the CONH moiety is in the β-orientation to the nortropane ring, that is as follows:

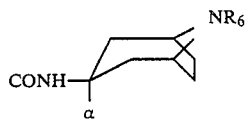

A preferred sub-group of compounds within formula (IV) is of formula (VI):

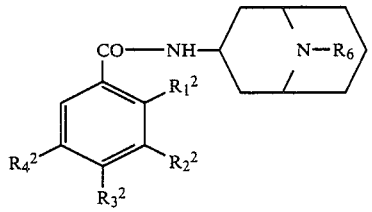 (VI)

Suitable and preferred values of $R_1{}^2$, $R_2{}^2$, $R_3{}^2$, $R_4{}^2$ and $R_6$ are as described under formulae (I) and (III).

$R_6$ is preferably benzyl optionally 4-substituted by fluoro, chloro or methyl.

It is preferred that the CONH moiety is in the β-orientation to the granatane ring, the β-orientation being the same as in the nortropane hereinbefore depicted.

Within each of formulae (V) and (VI), are sub-groups of compounds wherein $R_6$ is $C_{1-7}$ alkyl, such as $C_{5-7}$ alkyl, 2-thienylmethyl or $-(CH_2)_tR_8$ as defined in formula (I).

Within each of these latter sub-groups, there are compounds within formulae (V) and (VI) respectively wherein $R_6$ is $C_{5-7}$ alkyl or cyclohexylmethyl.

Within each of these same sub-groups, there are compounds within formulae (V) and (VI) respectively wherein $R_6$ is 2-thienylmethyl or $-(CH_2)_tR_8$ as defined in formula (I).

The invention also provides compounds within formula (I) of formula (VII):

wherein:
$R_1{}^3$ is $C_{1-6}$ alkoxy;
$R_3{}^3$ is amino or $C_{1-7}$ acylamino;
$R_4{}^3$ is $C_{1-6}$ alkylthio;
$p^1$ is 0 or 1;
and $R_6$ is as defined in formula (I).

Suitable values for $R_1{}^3$, $R_3{}^3$, $R_4{}^3$ and $R_6$ include those described in relation to formula (I) for $R_1$, $R_3$, $R_4$ and $R_6$ respectively.

$R_1{}^3$ is preferably methoxy.

$R_3{}^1$ is preferably amino or $C_{1-4}$ alkanoylamino, most preferably amino.

$R_4{}^3$ is preferably methylthio.

A particularly preferred benzamide moiety is formula (VII), therefore is wherein $R_1{}^3$ is methoxy, $R_3{}^3$ is amino and $R_4{}^3$ is methylthio.

There is a sub-group of compounds within formula (VII) of formula (VIII):

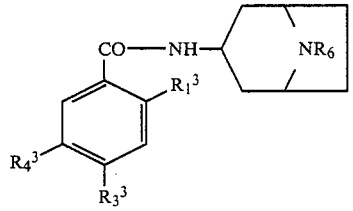 (VIII)

wherein $R_1{}^3$, $R_3{}^3$, $R_4{}^3$ and $R_6$ are as hereinbefore defined.

Suitable and preferred values of $R_1{}^3$, $R_3{}^3$, $R_4{}^3$ and $R_6$ are as hereinbefore described in relation to formula (VII).

$R_6$ is preferably benzyl.

It is preferred that the CONH moiety is in the β-orientation to the nortropane ring as hereinbefore depicted.

A preferred sub-group of compounds within formula (VII) is of formula (IX):

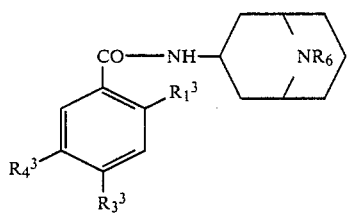 (IX)

wherein $R_1{}^3$, $R_3{}^3$, $R_4{}^3$ and $R_6$ are as hereinbefore defined.

Suitable and preferred values of $R_1{}^3$, $R_3{}^3$ and $R_4{}^3$ are as hereinbefore described in relation to formula (VII).

$R_6$ is preferably benzyl optionally substituted by fluoro, chloro or methyl.

It is preferred that the CONH moiety is in the β-orientation to the granatane ring, the β-orientation being the same as in the nortropane hereinbefore depicted.

Within each of formulae (VII) and (IX), are subgroups of compounds wherein $R_6$ is $C_{1-7}$ alkyl, such as $C_{5-7}$ alkyl, 2-thienylmethyl or $-(CH_2)_rR_8$ as defined in formula (I).

Within each of these latter sub-groups, there are compounds within formulae (VII) and (IX) respectively wherein $R_6$ is $C_{5-7}$ alkyl or cyclohexylmethyl.

Within each of these same sub-groups, there are compounds within formulae (VII) and (IX) respectively, wherein $R_6$ is 2-thienylmethyl or $-(CH_2)_rR_8$ as defined in formula (I).

Particularly suitable examples of the compounds of the present invention include those of the Examples hereinafter.

It will of course be realised that the compounds of the formula (I) and in particular compounds of formulae (II) and (VII) have chiral or prochiral centres, and thus are capable of existing in a number of stereoisomeric forms. The invention extends to each of the stereoisomeric forms of compounds of formulae (II) and (VII) and to compositions containing each of the stereoisomeric forms of compounds of formula (I) and a pharmaceutically acceptable carrier.

Compounds of the formula (I) are prepared by the reaction of a compound of formula (X):

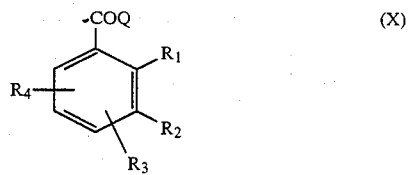

with a compound of formula (XI):

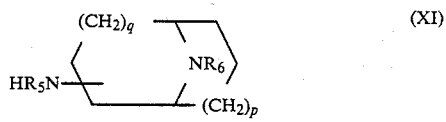

wherein:
Q is a leaving group; and the remaining variables are as hereinbefore defined; and thereafter if necessary converting a group $R_2$, $R_3$ or $R_4$ in the thus formed compound to another group $R_2$, $R_3$ or $R_4$ respectively; converting $R_6$ to (other) $R_6$; and optionally forming a pharmaceutically acceptable salt of the resultant compound of the formula (I).

The leaving group Q is a group that is readily displaceable by a nucleophile. Examples of such groups are hydroxy, halogen such as chloro and bromo and acyloxy such as $C_{1-4}$ alkanoyloxy $C_{1-4}$ alkoxycarbonyloxy and activated hydrocarbyloxy such as pentachlorophenoxy.

If a leaving group is hydroxy, then the reaction is preferably carried out in an inert non-hydroxylic solvent, such as benzene, toluene or diethyl ether in the presence of a dehydrating catalyst, such as a carbodiimide, for example dicyclohexylcarbodiimide. The reaction may be carried out at a non-extreme temperature such as $-10°$ to $100°$ C., for example $0°$ to $80°$ C.

If a leaving group is a halide, then the reaction is preferably carried out at a non-extreme temperature in an inert non-hydroxylic solvent, such as benzene, toluene or diethyl ether. It is also preferably carried out in the presence of an acid acceptor, such as an organic base, in particular a tertiary amine, such as triethylamine, trimethylamine, pyridine or picoline, some of which can also function as the solvent. Alternatively, the acid acceptor can be inorganic, such as calcium carbonate, sodium carbonate or potassium carbonate.

If a leaving group is acyloxy, then the reaction is preferably carried in substantially the same manner as if the leaving group were hydroxy. Suitable examples of acyloxy leaving groups include $C_{1-4}$ alkanoyloxy, mesyloxy, tosyloxy and triflate.

If a leaving group is $C_{1-4}$ alkoxycarbonyloxy, then the reaction is preferably carried out in an inert solvent, such as methylenechloride, at a non-extreme temperature in the presence of an acid acceptor, such as triethylamine.

If a leaving group is activated hydrocarbyloxy then the reaction is preferably carried out in an inert polar solvent, such as dimethylformamide. It is also preferred that the activated hydrocarbyloxy group is a pentachlorophenyl ester and that the reaction is carried out at ambient temperature.

Preferably Q is halogen, such as chloro.

The compounds of formula (X) and (XI) are either known compounds or can be prepared analogously to the preparation of structurally similar known compounds.

Compounds of formula (X) wherein $R_1$ and $R_2$ together form ethylenedioxy may be formed by heating a compound of formula (X) wherein $R_2$ is hydroxy and $R_1$ is replaced by an hydroxy group with dibromoethane in the presence of an inorganic base such as potassium hydroxide or potassium carbonate using ethanol-water as solvent.

Compounds of formula (X) wherein the third of $R_2$, $R_3$ and $R_4$ is aminosulphonyl may be formed from the corresponding chlorosulphonyl derivatives of the compound of formula (X) wherein $R_2$, $R_3$ or $R_4$ is replaced by hydrogen, with a suitable amine and ammonia.

The skilled man will appreciate that the choice or necessity of conversion of groups $R_2$, $R_3$ and/or $R_4$ to other groups $R_2$ and $R_3$ and/or $R_4$ will be dictated by the nature and position of substituents $R_1$, $R_2$, $R_3$ and $R_4$.

It will be apparent that compounds of the formula (I) containing an $R_2$, $R_3$, $R_4$ or $R_6$ group which is convertible to another $R_2$, $R_3$ & $R_4$ group or to another $R_6$ group are useful intermediates. A number of such conversions is possible not only for the end compounds of formula (I), but also for their intermediates as follows:

(a) an hydrogen substituent is convertible to a nitro substituent by nitration;

(b) a nitro substituent is convertible to an amino substituent by reduction;

(c) a $C_{1-4}$ acylamino substituent is convertible to an amino substituent by deacylation;

(d) an amino substituent is convertible to a $C_{1-4}$ acylamino substituent by acylation;

(e) a hydrogen substituent is convertible to a halogen substituent by halogenation.

(f) a $C_{1-6}$ alkylthio or $C_{1-6}$ alkylsulphinyl substituent is convertible to a $C_{1-6}$ alkylsulphinyl or a $C_{1-6}$ alkylsulphinyl or a $C_{1-6}$ alkylsulphonyl substituent respectively by oxidation.

Conversions (a) to (f), are only exemplary and are not exhaustive of the possibilities.

In regard to (a), nitration is carried out in accordance with known procedures.

In regard to (b), the reduction is carried out with a reagent suitable for reducing nitroanisole to aminoanisole.

In regard to (c), deacylation is carried out by treatment with a base, such as an alkali metal hydroxide.

In regard to (d), the acylation is carried out with an acylating agent, such as the corresponding acid or acid chloride. Formylation is carried out with the free acid.

In regard to (e), halogenation is carried out with conventional halogenating agents.

In regard to (f), oxidation is carried out at below ambient temperatures in a non-aqueous solvent, such as a chlorinated hydrocarbon, in the presence of an organic peracid, such as 3-chloroperbenzoic acid, or in water in the presence of a soluble strong inorganic oxidant, such as an alkali metal permananate or in aqueous hydrogen peroxide.

It will be appreciated that, $R_6$ which is optionally substituted benzyl as hereinbefore defined, may be replaced by another group $R_6$.

Such $R_6$ benzyl groups may be removed for example when $R_2$, $R_3$ or $R_4$ is not halogen by conventional transition metal catalysed hydrogenolysis to give compounds of the formula (XII):

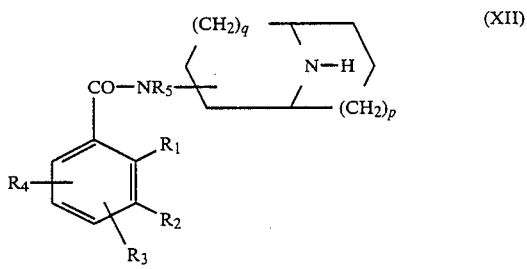

wherein the variable groups are as defined in formula (I).

An optional process step in the preparation of a compound of the formula (I) therefore comprises the reaction of a corresponding compound of the formula (XII) as hereinbefore defined with a compound $Q_2R_6$ wherein $R_6$ is as defined in formula (I) and $Q_2$ is a leaving group, and optionally forming a pharmaceutically acceptable salt of the resulting compound of the formula (I).

Suitable value for $Q_2$ include groups readily displaced by nucleophiles such as Cl, Br, I, $OSO_2CH_3$ or $OSO_2C_6H_4pCH_3$.

Favoured values for $Q_2$ include Cl, Br and I.

Particularly suitably the compound $Q_3R_6$ is a benzyl halide such as the bromide or chloride.

The reaction may be carried out under conventional alkylation conditions for example in an inert solvent such as dimethylformamide in the presence of an acid acceptor such as potassium carbonate. Generally the reaction is carried out at non-extreme temperature such as at ambient or at a slightly elevated temperature.

Converting $R_6$ to another $R_6$ in the compound of the formula (XI) before coupling with the compound of the formula (X) or its derivative is preferred. Such interconversions are affected conveniently under the above conditions. It is desirable to protect the amine function with a group readily removable by acidolysis such as a $C_{2-7}$ alkanoyl group before $R_6$ interconversion.

It will be realised that in the compound of the formula (I) the —CO—NR$_5$— linkage may have an $\alpha$ or $\beta$ orientation with respect to the ring of the bicyclic moiety to which it is attached. A mixture of $\alpha$ and $\beta$ isomers of the compound of the formula (I) may be synthesised nonstereospecifically and the desired isomer separated conventionally therefrom e.g. by chromatography; or alternatively the $\alpha$ and $\beta$ isomer may if desired be synthesised from the corresponding $\alpha$ or $\beta$ form of the compound of the formula (XI).

Synthesis from the corresponding $\alpha$ or $\beta$ isomer of the compound of the formula (XI) is in general preferred.

The $\alpha$ or $\beta$ form of the compound of the formula (XI) may if desired be prepared by known stereospecific processes, such as those leading to the $\alpha$ or $\beta$ isomers of the compound of the formula (XI) depicted in the Scheme and described in the Descriptions hereinafter.

Scheme 1

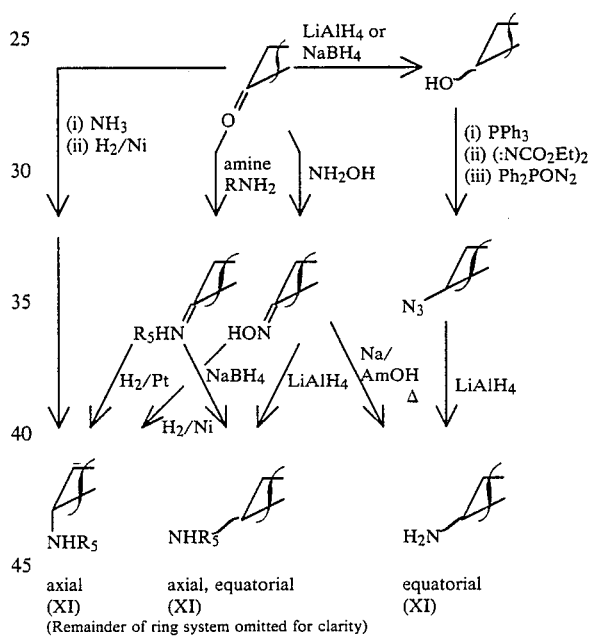

axial    axial, equatorial    equatorial
(XI)    (XI)    (XI)
(Remainder of ring system omitted for clarity)

The invention provides a process for the preparation of a compound of formula (II) which process comprises reacting a compound of formula (XIII):

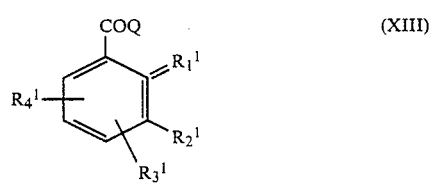

with a compound of formula (XIV)

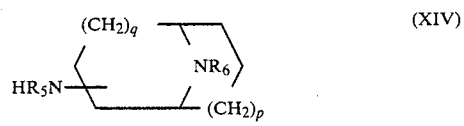

wherein the variable groups are as hereinbefore defined; and thereafter converting a group $R_2^1$, $R_3^1$ or $R_4^1$ in the thus formed compound to another group $R_2^1$, $R_3^1$, $R_4^1$ respectively; converting $R_6$ to (other) $R_6$; and optionally forming a pharmaceutically acceptable salt of the resultant compound of formula (I).

The process details for this reaction and subsequent interconversions are essentially as hereinbefore described with reference to the preparation of compounds of the formula (I).

The invention further provides an optional process for the preparation of a compound of formula (II) which comprises the reaction of a compound of formula (XV):

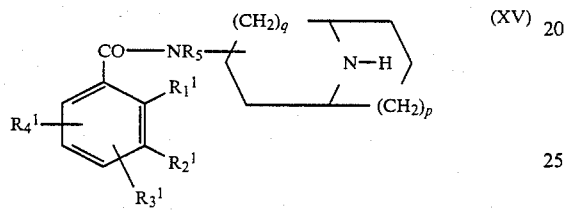

with $Q_2R_6$ as hereinbefore defined.

The invention further provides a process for the preparation of a compound of formula (VII) which process comprises reacting a compound of formula (XVI):

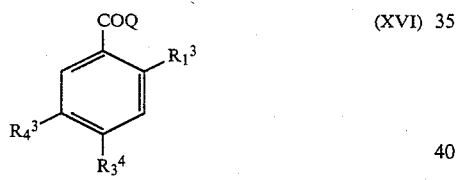

with a compound of formula (XVI):

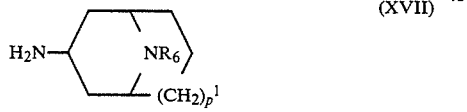

wherein $R_3^4$ is $R_3^3$ or a nitro group; the variable groups are as hereinbefore defined; and thereafter if necessary converting a group $R_2^3$, $R_3^4$ or $R_4^3$ in the thus formed compound to another $R_2^3$, $R_3^3$ or another $R_4^3$ group respectively; converting $R_6$ to (other) $R_6$, and optionally forming a pharmaceutically acceptable salt of the resultant compound of formula (I).

The process details for this reaction and subsequent interconversions are essentially as hereinbefore described with reference to the preparation of compounds of formula (I).

The invention further provides an optional process for the preparation of a compound of formula (VII) which process comprises the reaction of a compound of formula (XVIII):

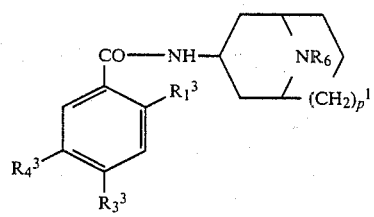

with $Q_2 R_6$ as hereinbefore defined.

The following examples illustrate the preparation of compounds of the invention and the following descriptions illustrate the preparation of intermediates thereto.

DESCRIPTION 1

Methyl-4-amino-2-methoxy benzoate (D1)

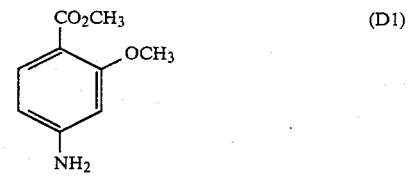

To a mixture of p-aminosalicylic acid (60 g, 0.39 mole) and potassium hydroxide (55.0 g, 0.98 mole) in dry acetone (1200 ml) dimethyl sulphate (88 ml) was added dropwise with vigorous stirring at room temperature. The mixture was further stirred for 3 hours. The solvent was then evaporated under reduced pressure to leave a solid residue. Water (800 ml) was added and the solid filtered. Washing with water (1 h) gave the title compound (66 g; 86%) m.p. 154°–156°.

DESCRIPTION 2

Methyl-4-amino-2-methoxy-5-thiocyano-benzoate (D2)

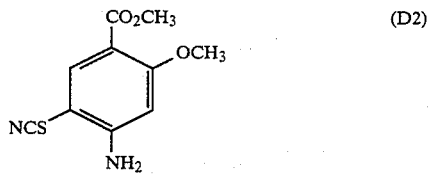

Methyl-4-amino-2-methoxy benzoate (14.0 g, 0.0774 mole) was dissolved in methanol (400 ml) containing potassium thiocyanate (15.0 g). Bromine (4.25 ml) in methanol (20 ml) was added dropwise with stirring at room temperature over 1 hr. The solution was stirred for a further hour then poured into water (1 L). The precipitate was filtered and washed with water and dried in vacuo to yield the title compound (14.58 g; 79%) mp 184°–185° (i.r. SCN 2150 cm$^{-1}$ (s)).

DESCRIPTION 3

4-Amino-2-methoxy-5-methylthiobenzoic acid (D3)

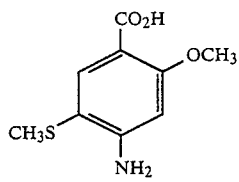

Methyl-4-amino-2-methoxy-5-thiocyanobenzoate (50.18 g, 0.211 mole) was dissolved in methanol (1.5 L) containing potassium hydroxide (70 g). The solution was warmed to 60° for 1 hour then methyl iodide (20 ml) was added dropwise over 2 hours. The mixture was heated to reflux for 1 hour and then evaporated to ¼ volume. Inorganic salts were filtered and the filtrate evaporated in vacuo to dryness. The solid was dissolved in water (200 ml) and filtered (1.2 g-methyl ester of title compound). Acidification of the filtrate gave the title compound which was filtered, washed with water and dried in vacuo. (33.0 g; 73%) mp 152°–154°.

DESCRIPTION 4

5-Chlorosulphonyl-2,3-dimethoxybenzoic acid (D4)

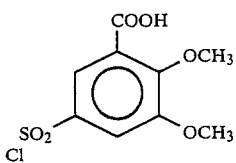

2,3-Dimethoxybenzoic acid (5 g) was added in small portions to chlorosulphonic acid (10 mls) keeping the temperature of the mixture below 5° C. The reaction mixture was then warmed to 55° C. and maintained at this temperature for 2 hours before cooling and pouring into ice-water.

The precipitated product was filtered and dried in vacuo to give 5-chlorosulphonyl-2,3-dimethoxybenzoic acid (3.8 g, 50%).

DESCRIPTION 5

Bis(2,3-dimethoxybenzoic acid)-5-disulphide (D5)

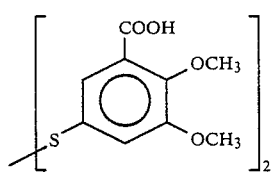

Tin (11) chloride (26 g) was added in portions to a suspension of 5-chlorosulphonyl-2,3-dimethoxy-benzoic acid (5.5 g) in a mixture of concentrated hydrochloric acid (13 mls) and water (5 mls) and the mixture was stirred for 4 hours.

The reaction mixture was filtered, washed with 5N hydrochloric acid and dried over potassium hydroxide in vacuo to give bis(2,3-dimethoxybenzoic acid)-5-disulphide (4.2 g).

DESCRIPTION 6

2,3-Dimethoxy-5-methylthiobenzoic acid (D6)

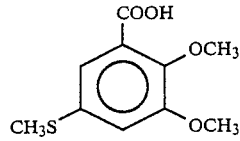

The disulphide (D5) (4.0 g) was heated under reflux in 10% sodium hydroxide solution (100 ml) for 1 hour, before filtration of the hot solution. The filtrate was allowed to cool before the addition of dimethyl sulphate (3 mls). After standing at room temperature overnight the solution was acidified with 5N hydrochloric acid, filtered and dried over potassium hydroxide in vacuo to give 2,3-dimethoxy-5-methylthiobenzoic acid (1.2 g, 28%) m.pt. 139°–141° C.

EXAMPLE 1

4-Amino-2-methoxy-5-methylthio-N-[3-β-(8-benzyl-8-azabicyclo(3,2,1)octyl)]benzamide (E1)

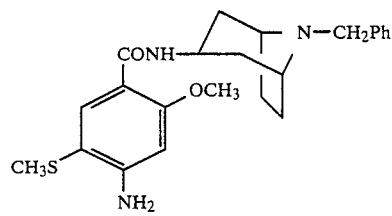

4-Amino-2-methoxy-5-methylthiobenzoic acid (2.39 g, 0.001122 mole) was dissolved in anhydrous dimethylformamide (30 ml) containing triethylamine (1.13 g, 1.6 ml) and cooled to 3°. Ethyl chloroformate (1.21 g, 1.07 ml) was added dropwise at 0°–3° C. After a further 15 minutes 3-β-amino-8-benzyl-8-azabicyclo(3,2,1)octane (2.4 g, 0.001122 moles) in anhydrous dimethylformamide (10 ml) was added slowly in one portion. The mixture was stirred and allowed to reach ambient temperatures overnight.

The mixture was evaporated in vacuo, and the residual semi-solid treated with water (15 ml) and dilute sodium hydroxide (10 ml). The whole was extracted with ethyl acetate (3×150 ml). The combined organic extract were dried (solid potassium carbonate) filtered and evaporated in vacuo. Recrystallisation from ethyl acetate gave the title compound (1.85 g=40%) as colourless microcrystals mp 215°.

| n.m.r. CDCl₃. | | |
|---|---|---|
| δ | 8.5 | (S, 1H, aromatic 6H) |
| | 7.65–7.25 | (M, 6H, CONH + aromatic Ph-CH₂) |
| | 6.24 | (S, 1H, aromatic 3H) |
| | 4.70 | (broad exchangeable, 2H, NH₂) |
| | 4.65–4.15 | (M, 1H, 3 α H) |
| | 3.80 | (S, 3H, O—OCH₃) |
| | 3.60 | (S, 2H, Ph-CH₂.N) |
| | 3.25 | (broad, 2H, ╲C—H × 2) ╱ |
| | 2.25 | (S, 3H, CH₃S—Ar) |

| n.m.r. CDCl₃ |
| --- |
| 2.25–1.45 (M, 8H, (CH₂)₄) |

EXAMPLE 2

4-Amino-2-methoxy-5-methylthio-[N-(9-(4¹-fluorobenzyl)-9-azabicyclo(3.3.1)non-3β-yl)]benzamide (E2)

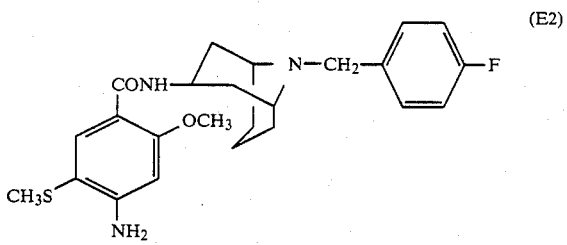

A solution of 4-amino-5-thiomethyl-2-methoxybenzoic acid (0.5 g) and triethylamine (0.5 ml) in dichloromethane (50 ml) was cooled to 0° C. Ethyl chloroformate (0.26 g) was added and the reaction mixture stirred at 0° C. for 2 hours. β-Amino-9(4-fluorobenzyl)-9-azabicyclo(3.3.1)nonane (0.58 g) in dichloromethane (50 ml) was added and the solution stirred at room temperature for 24 hours. It was then diluted with water, basified with potassium carbonate and the dichloromethane separated and dried. Evaporation of the dichloromethane gave a crude product which was chromatographed on silica gel using ethyl acetate as eluant to give the title compound (0.7 g, 67%) m.p. 194°–6°.

EXAMPLE 3

2,3-Dimethoxy-5-methylthio-N[3β(8-benzyl-8-azabicyclo[3.2.1]octyl)]benzamide hydrochloride (E3)

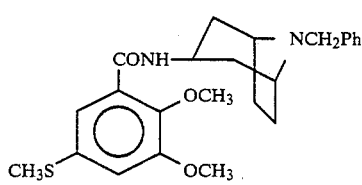

2,3-Dimethoxy-5-methylthiobenzoic acid (1.13 g) was suspended in dry dichloromethane (30 ml) with oxalyl chloride (0.44 ml) and dry dimethylformamide (0.5 ml) added. The mixture was stirred at room temperature until it became homogeneous.

The solution was cooled to 0° C. and kept below this temperature during the dropwise addition of triethylamine (2 ml) in dry dichloromethane (10 ml), followed by the dropwise addition of 3β-amino-8-benzyl-8-azabicyclo[3.2.1]octane (1.0 g) in dry dichloromethane (10 ml).

The reaction mixture was allowed to warm to room temperature before being shaken with 10% sodium hydroxide solution (10 ml). The organic layer was dried over anhydrous sodium sulphate, filtered and the solvent was removed in vacuo to give an oil (2.3 g). Purification by column chromatography (silica, chloroform) gave an oil (1.7 g, 85%) from which the hydrochloride salt was prepared m.pt. 217°–217,5° C., $C_{24}H_{31}N_2SClO_3$ requires C, 62.27; H, 6.7; N, 6.05%. Found C, 62.10; H, 6.76; N, 5.97. nmr (D₂O) τ2.45–2.65 (6H, M, NCH₂C₆H₅ and —CONH—), 3.0 (1H, d, aromatic H̲), 3.1 (1H, d, aromatic H̲), 5.8 (2H, S, NCH₂C̲₆H₅), 6.0 (2H, M, bridgehead H̲'s), 6.2 (3H, S, —OCH̲₃), 6.3 (3H, S, —OCH̲₃), 7.6–8.35 (11H, S and M, —SCH̲₃ and methylene H̲'s).

EXAMPLE 4

2,3-dimethoxy-5-methylthio-[N-(9-(4¹-fluorobenzyl)-9-azabicyclo(3.3.1)non-3β-yl)]benzamide (E4)

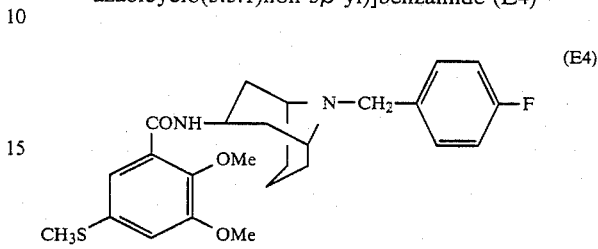

2,3-Dimethoxy-5-methylthiobenzoic acid (1 g) and triethylamine (1 ml) in dichloromethane (50 ml) was cooled to 0° C. Ethyl chloroformate (0.48 g) was added and the reaction mixture stirred at 0° C. for 2 hours. β-Amino-9-(4¹-fluorobenzyl)-9-azabicyclo(3.3.1)nonane (1.1 g) in dichloromethane (50 ml) was added and the solution stirred at room temperature for 24 hours. It was then diluted with water, basified with potassium carbonate and the dichloromethane separated and dried. Evaporation of the dichloromethane gave a crude product which was chromatographed on silica gel using ethyl acetate as eluant to give the title compound (0.5 g, 25%) m.p. 122°–4°.

PHARMACOLOGICAL DATA

The results in the following table are on illustration of the anti-psychotic activity of the present compounds as shown by Inhibition of Apomorphine Induced Climbing in the Mouse, a standard test.

Inhibition of apomorphine induced climbing in the mouse

The test is based on that described by Protais, P., Constantin, J. and Schwartz J. C. (1976), Psychopharmacology, 50, 1–6.

When mice are given a dose of 1 mg/kg apomorphine and then placed in an enclosed environment, such as an inverted wire cage, they are seen to climb around the walls. This behavioural phenomenon is thought to be a consequence of the stimulation of post-synaptic Dopamine (D.A.) receptors in the nucleus accumbens. Inhibition of apomorphine induced climbing is therefore indicative of post-synaptic D.A. receptor blockade in the accumbens.

Groups of 10 male CD1 mice, weighing 25–30 g were pre-treated orally with either graded doses of the test compound or vehicle, at appropriate time intervals before the subcutaneous administration of a sub-maximal dose of apomorphine (1 mg/kg). Immediately after the apomorphine injection the mice were placed in wire 'climbing cages' and each animal was scored for climbing behaviour at 10 and 20 minutes post apomorphine as follows:

Four paws on cage floor=0
Fore paws on cage wall=1
Four paws on cage wall=2

The test compound was administered subcutaneously 30 minutes prior to administration of apomorphine.

The total score was calculated for each group of mice and expressed as a percentage inhibition of climbing.

$$\% \text{ inhibition} = 100 - \frac{\text{Total score for test compound}}{\text{Total score for apomorphine control}}$$

ED50's and fiducial limits were calculated according to the method of Litchfield and Wilcoxon, the ED50 being the dose that produced a 50% inhibition of apomorphine—induced climbing.

The table shows the results obtained.

| Compound of Example No. | ED$_{50}$ mg/kg |
| --- | --- |
| 1 | 0.66 |
| 2 | 0.32 |
| 3 | 0.44 |
| 4 | 0.56 |

Toxicity

No toxic effects were observed in the test reported above.

I claim:

1. A compound of formula (VII) or a pharmaceutically acceptable salt and/or solvate and/or N-oxide thereof:

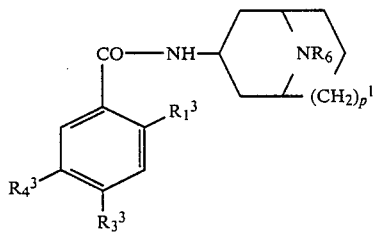

(VII)

wherein:
$R_1^3$ is $C_{1-6}$ alkoxy;
$R_3^3$ is amino or $C_{1-7}$ acylamino;
$R_4^3$ is $C_{1-6}$ alkylthio;
$p^1$ is 0 or 1;
and $R_6$ is $C_{1-7}$ alkyl or a group —$(CH_2)_sR_7$ where s is 0 to 2 and $R_7$ is a $C_{3-8}$ cycloalkyl group, or a group —$(CH_2)_tR_8$ where t is 1 or 2 and $R_8$ is $C_{2-5}$ alkenyl or a phenyl group optionally substituted by one or two substituents selected from $C_{1-6}$ alkyl, $C_{1-4}$ alkoxy, trifluoromethyl and halogen.

2. A compound according to claim 1 of formula (IX):

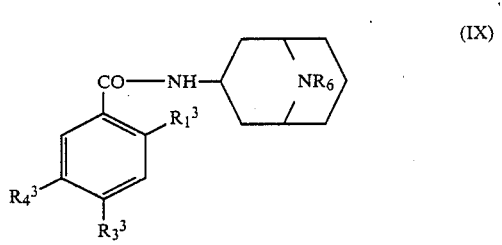

(IX)

3. A compound according to claim 1 wherein $R_1^3$ is methoxy, $R_3^3$ is amino and $R_4^3$ is methylthio.

4. A compound according to claim 1 wherein $R_6$ is —$(CH_2)_t R_8$.

5. A compound according to claim 2 wherein $R_6$ is benzyl p-substituted by fluoro, chloro or methyl.

6. 4-Amino-2-methoxy-5-methyltho-[N-(9-(4$^1$-fluorobenzyl)-9-azabicyclo(3.3.1)non-3β-yl)]benzamide.

7. A compound according to claim 5, wherein the CO—NH moiety is in a β-orientation to the nortropane/granatane ring.

8. 4-Amino-2-methoxy-5-methylthio-N-[3-β-(8-benzyl-azabicyclo(3,2,1)octyl)]benzamide.

9. A pharmaceutical composition for the treatment of pychosis, comprising an effective amount of a compound according to claim 1 or a pharmaceutically acceptable salt thereof, and a pharmaceutically acceptable carrier.

10. A method of treatment of pychosis in mammals, including humans, which comprises administering to the sufferer an effective amount of a compound according to claim 1 or a pharmaceutically acceptable salt thereof.

* * * * *